(12) United States Patent
Geissler et al.

(10) Patent No.: US 6,353,136 B1
(45) Date of Patent: Mar. 5, 2002

(54) PROCESS FOR PREPARING AROMATIC AMINES IN THE PRESENCE OF PALLADAPHOSPHACYCLOBUTANE CATALYSTS

(75) Inventors: Holger Geissler, Mainz; Steffen Haber, Landau/Pfalz; Stefan Scherer, Buettelborn; Andreas Meudt, Floersheim-Weilbach; Frank Vollmueller, Mainz, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/658,830

(22) Filed: Sep. 8, 2000

(30) Foreign Application Priority Data

Sep. 9, 1999 (DE) .......................................... 199 42 961

(51) Int. Cl.$^7$ ............................................. C07C 211/00
(52) U.S. Cl. ........................ 564/405; 564/445; 546/192; 546/214; 548/343.5
(58) Field of Search ................................ 546/192, 214; 564/405, 445; 548/343.5

(56) References Cited

U.S. PATENT DOCUMENTS 5,831,128 A    11/1998  Beller et al.
6,084,114 A    7/2000   Geissler et al.

FOREIGN PATENT DOCUMENTS

| DE | 196 47 584 | 5/1998 |
|----|------------|--------|
| DE | 196 50 213 | 6/1998 |
| EP | 0 802 173  | 10/1997 |

OTHER PUBLICATIONS

A.S. Guram, et al., Angew. Chem. 1995, 107, 1459.

Primary Examiner—Samuel Barts
(74) Attorney, Agent, or Firm—Scott E. Hanf

(57) ABSTRACT

Aromatic amines of the formula (I)

$$Ar-[NR^6R^7]_n \qquad (I)$$

are prepared by reacting a haloaromatic of the formula (II)

$$Ar-Hal \qquad (II)$$

with an amine of the formula (III)

$$R^6R^7NH \qquad (III)$$

in the presence of a palladaphosphacyclobutane and a base and in the presence or absence of an ionic halide in a solvent at temperatures of from 20 to 200° C.

11 Claims, No Drawings

PROCESS FOR PREPARING AROMATIC AMINES IN THE PRESENCE OF PALLADAPHOSPHACYCLOBUTANE CATALYSTS

BACKGROUND OF THE INVENTION

The present invention relates to a novel process for preparing aromatic amines using palladaphosphacyclobutanes.

Aromatic amines, in particular substituted anilines, are of great industrial importance as precursors for dyes, fine chemicals, agrochemicals and intermediates for active compounds.

The preparation of substituted anilines is generally carried out industrially by nitration of a corresponding aromatic and subsequent hydrogenation. Since nitrations take place under drastic reaction conditions, many anilines having a complex substitution pattern can be prepared only with difficulty, if at all, by this route.

Palladium-catalyzed aminations of iodoaromatics, bromoaromatics and chloroaromatics leading to substituted anilines are described in A. S. Guram et al., Angew. Chem. 1995, 107, 1459. These reactions are carried out under comparatively mild reaction conditions and can therefore also be used for the synthesis of anilines having a complex substitution pattern. The iodoaromatics and bromoaromatics used as starting materials are significantly more expensive and less readily available than the chloroaromatics.

DE-A1-196 50 213 discloses a process for the amination of chloroaromatics using trans-di-μ-acetatobis(o-(di-o-tolylphosphino)benzyl)dipalladium, if desired in the presence of halide cocatalysts. In general, 1 mol % of catalyst (corresponding to 2 mol % of Pd) is used.

Particularly in the case of chloroaromatics, large amounts of catalyst, in general from 1 to 5 mol %, are usually added in order to achieve industrially useful conversions. Owing to the complexity of the reaction mixture, simple recycling of the catalyst is not possible, so that the catalyst costs generally stand in the way of industrial implementation.

SUMMARY OF THE INVENTION

There is therefore a great need for a process for preparing aromatic amines which does not have the abovementioned disadvantages, is suitable for industrial implementation and gives aromatic amines in high yield and purity.

This object is surprisingly achieved by the use of particular palladaphosphacyclobutanes as catalysts.

DESCRIPTION OF THE PREFERRED EMBODIMENTS

The present invention provides a process for preparing aromatic amines of the formula (I)

where n is 1, 2 or 3,

Ar is unsubstituted or substituted phenyl, furanyl, pyrryl, pyridinyl, naphthyl or quinolinyl, where the substituents are 1, 2, 3, 4, 5 or 6, preferably 1, 2 or 3, in number and are selected from the group consisting of $C_1$–$C_8$-alkyl, $C_3$–$C_8$-cycloalkyl, $C_1$–$C_8$-alkoxy, $C_1$–$C_8$-acyloxy, $C_6$–$C_{10}$-aryloxy, $C_6$–$C_{10}$-aryl, benzyl, fluorine, chlorine, bromine, OH, $NO_2$, $OSO_2CF_3$, CN, COOH, CHO, $SO_3H$, $SO_2R$, SOR, where R is $C_1$–$C_4$-alkyl, $C_6$–$C_{10}$-aryl or benzyl, $NH_2$, NH—$C_1$–$C_8$-alkyl, N—$(C_1$–$C_8$-alkyl$)_2$, $CF_3$, NHCO—$C_1$–$C_4$-alkyl, N—$C_1$–$C_4$-alkyl-CO—$C_1$–$C_4$-alkyl, COO—$C_1$–$C_8$-alkyl, $CONH_2$, CO—$C_1$–$C_8$-alkyl, NHCOH, NCOO—$C_1$–$C_4$-alkyl, CO-phenyl, COO-phenyl, CHCH—$CO_2$—$C_1$–$C_8$alkyl, $CHCHCO_2H$, PO-phenyl$_2$, PO—$(C_1$–$C_4$-alkyl$)_2$, 5-membered heteroaryl and 6-membered heteroaryl in each case containing O, S and/or N as heteroatoms; and $R^6$ and $R^7$ are, independently of one another, hydrogen, $C_1$–$C_{12}$-alkyl, $C_1$–$C_{12}$-hydroxyalkyl, unsubstituted or substituted phenyl, or $C_3$–$C_8$-cycloalkyl, or $R^6$ and $R^7$ together with the N atom form a 5- or 6-membered aliphatic or aromatic ring which may contain 1 or 2 further atoms selected from the group consisting of N, O and S as heteroatoms, by reacting haloaromatics of the formula (II)

where Hal is Cl, Br or I,
with an amine of the formula (III)

wherein the reaction is carried out in the presence of a palladaphosphacyclobutane of the formula (IV)

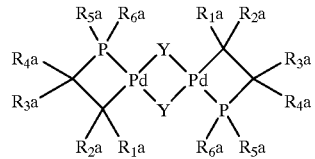

where $R^{1a}$, $R^{2a}$ are, independently of one another, hydrogen, $C_1$–$C_4$-alkyl, $C_3$–$C_{12}$-cycloalkyl, $C_1$–$C_4$-alkoxy, fluorine, N—$(C_1$–$C_4$-alkyl$)_2$, $CO_2$—$C_1$–$C_4$-alkyl, OCO—$C_1$–$C_4$-alkyl or substituted or unsubstituted aryl, $R^{3a}$, $R^{4a}$, $R^{5a}$ and $R^{6a}$ are, independently of one another $C_1$–$C_8$-alkyl, $C_3$–$C_{12}$cycloalkyl, substituted or unsubstituted aryl;

or $R^{1a}$ and $R^{2a}$, or $R^{2a}$ and $R^{3a}$, or $R^{3a}$ and $R^{4a}$ together form an aliphatic ring having from 4 to 10 carbon atoms, or $R^{5a}$ and $R^{6a}$ together with the P atom form a saturated or unsaturated 4- to 9-membered ring, or $R^{4a}$ and $R^{5a}$ form a bridging 1,ω-alkanediyl chain having from 2 to 7 carbon atoms, and Y is an anion of an inorganic or organic acid, an α,γ-diketo compound or a 5- to 6-membered nitrogen-containing heterocycle, in the presence of a base and in the presence or absence of an ionic halide in a solvent at temperatures of from 20 to 200° C.

The synthesis of the palladaphosphacyclobutanes is described in DE-A1-196 47 584. Preference is given to compounds of the formula (IV) in which $R^{1a}$ and $R^{2a}$ are, independently of one another, hydrogen, methyl, ethyl, cyclopentyl, cyclohexyl, methoxy, ethoxy, fluorine, phenyl, tolyl or naphthyl;

$R^{3a}$ and $R^{4a}$ are, independently of one another, $C_1$–$C_4$-alkyl, $C_5$–$C_6$-cycloalkyl, substituted or unsubstituted $C_6$–$C_{10}$-aryl or $R^{3a}$ and $R^{4a}$ together form an aliphatic ring having from 5 to 6 carbon atoms;

$R^{5a}$ and $R^{6a}$ are, independently of one another, $C_1$–$C_4$-alkyl, $C_5$–$C_6$-cycloalkyl, phenyl, naphthyl, anthracenyl, each of which may be unsubstituted or substituted by from 1 to 3 $CF_3$—, $C_1$–$C_4$-alkyl or $C_1$–$C_4$-alkoxy groups;

and Y is acetate, propionate, benzoate, chloride, bromide, iodide, fluoride, sulfate, hydrogensulfate, nitrate, phosphate, trifluoromethanesulfonate, tetrafluoroborate, tosylate, mesylate, acetylacetonate, hexafluoracetylacetonate or pyrazolyl.

Particular preference is given to compounds of the formula (IV) in which $R^{1a}$ and $R^{2a}$ are, independently of one another, hydrogen or methyl;

$R^{3a}$ and $R^{4a}$ are, independently of one another, methyl, ethyl or phenyl;

$R^{5a}$ and $R^{6a}$ are, independently of one another, phenyl, naphthyl, o-trifluoromethylphenyl, o-trifluoromethyl-p-tolyl, o-trifluoromethyl-p-methoxyphenyl, o-methoxyphenyl, o,p-dimethoxyphenyl, o,o,p-trimethoxyphenyl, anthracenyl, tert-butyl, n-butyl, isopropyl, isobutyl, cyclohexyl or 1-methylcyclohexyl.

Very particular preference is given to the following compounds of the formula (IV):

trans-di-μ-acetatobis[2-[bis(1,1-dimethylethyl)phosphino]-2-methylpropyl-C,P]dipalladium(II), trans-di-μ-acetatobis[2-[1,1-dimethylethyl)phenylphosphino]-2-methylpropyl-C,P]dipalladium(II), trans-di-μ-chlorobis[2-[bis(1,1-dimethylethyl)phosphino]-2-methylpropyl-C,P]dipalladium(II), trans-di-μ-chlorobis[2-[(1,1-dimethylethyl)phenylphosphino]-2-methylpropyl-C,P]dipalladium(II), trans-di-μ-bromobis[2-[bis(1,1-dimethylethyl)phosphino]-2-methylpropyl-C,P]dipalladium(II) and trans-di-μ-bromobis[2-[(1,1-dimethylethyl)phenylphosphino]-2-methylpropyl-C,P]dipalladium(II).

The palladium catalysts are synthesized before the actual reaction, but can also be generated in situ, as described, for example, in EP-A1-0802173. However, in the case of a prolonged reaction time, the in-situ mixtures (molar ratio Pd:P=1:1) prove to have little stability and frequently lead to deposition of palladium. This disadvantage is surprisingly overcome by the use according to the invention of previously prepared palladaphosphacyclobutanes.

Palladaphosphacyclobutanes generally have a dimeric structure. However, in the case of particular compounds (e.g. Y=acetylacetone, hexafluoracetylacetone) monomeric, oligomeric or even polymeric structures may be present.

During the catalysis cycle, the dimeric structure is broken up by bridge cleavage reactions with inorganic and organic nucleophiles, so that the mononuclear complexes of the formulae (V) and (VI)

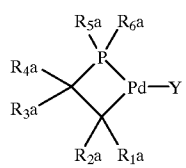

(III)

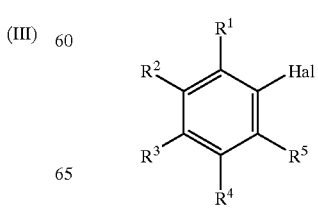

(III)

may be the actual catalytically active species. The complexes of the formulae (V) and (VI) are in equilibrium with the dimers used and are uncharged or anionic. The mononuclear complex of the formula (V) may have further donor ligands on the palladium atom.

The palladaphosphacyclobutanes used have very high activity and surprisingly high stability.

The stability of the palladaphosphacyclobutanes in solution can be increased further by addition of alkali metal salts, alkaline earth metal salts and transition metal salts of transition groups VI to VII. The addition of ionic halides and pseudohalides (e.g. $CN^-$) in particular results in significant yield increases and improvements in the life of the homogeneous catalyst in the reaction of chloroaromatics.

The ionic halide is preferably an alkali metal, ammonium, alkylammonium, alkylolammonium or phosphonium halide, in particular an alkali metal or ammonium halide, where halide is chloride, bromide or iodide, in particular bromide or chloride. Examples are ammonium bromide, lithium bromide, sodium bromide, potassium bromide, tetrabutylphosphonium bromide, ammonium chloride, dimethylammonium chloride, diethanolammonium chloride, lithium chloride, sodium chloride, potassium chloride, tetrabutylphosphonium chloride, ammonium iodide, lithium iodide, sodium iodide, potassium iodide and/or tetrabutylphosphonium iodide, in particular lithium chloride, ammonium chloride, dimethylammonium chloride, and/or diethanolammonium chloride.

The ionic halide is preferably used in an amount of from 0.1 to 100 mol %, in particular from 3 to 50 mol %, based on the haloaromatic used. In the form of a liquid salt, it can also serve as solvent.

Owing to the activity and stability of the catalyst, it is possible to use very small amounts of catalyst, so that the catalyst costs are no longer cost-limiting for the corresponding process, in contrast to conventional processes.

The catalyst can be used in amounts of from 0.001 to 5 mol %, preferably from 0.005 to 2 mol %, in particular from 0.01 to 0.9 mol %, based on the haloaromatic of the formula (II).

Preferred haloaromatics of the formula (II) are those of the formulae (II a), (II b), (II c) and (II d)

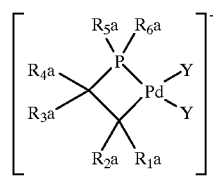

(II a)

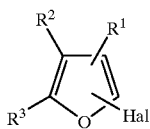
(II b)

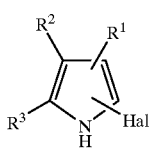
(II c)

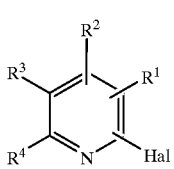
(II d)

where

Hal is as defined above $R^1$ to $R^5$ are identical or different and are each hydrogen, $C_1$–$C_4$-alkyl, $C_5$–$C_6$-cycloalkyl, $C_1$–$C_4$-alkoxy, $C_1$–$C_6$-acyloxy, phenoxy, phenyl, fluorine, chlorine, OH, $NO_2$, CN, COOH, NH—$C_1$–$C_4$-alkyl, N($C_1$–$C_4$-alkyl)$_2$, $NH_2$, COO—$C_1$–$C_4$-alkyl, CO—$C_1$–$C_4$-alkyl, $CF_3$, $SO_3H$, $SO_2R$, where R is methyl, ethyl or phenyl.

The radical Hal can be located at any position on the aromatic ring.

Preferred amines of the formula (III) are ones in which $R^6$ and $R^7$ are identical or different and are each hydrogen, $C_1$–$C_6$-alkyl, $C_1$–$C_6$-hydroxyalkyl, phenyl or $C_5$–$C_6$-cycloalkyl, or $R^6$ and $R^7$ together with the N atom form a piperazine, piperidine, morpholine, imidazole, pyrazole or pyrrolidine ring.

The process of the invention makes it possible to prepare, for example, compounds such as arylpiperazines, arylpiperidines, aryldibutylamines, arylmorpholines, arylphenylmethylamines, aryldiethylamines and aryldiphenylamines, where aryl is preferably phenyl, methoxyphenyl, trifluoromethylphenyl, acetylphenyl, fluorophenyl, difluorophenyl, chlorophenyl, methylphenyl, pyridyl or naphthyl, in a simple manner.

The amine of the formula (III) is advantageously used in an amount of from 1 to 1.3 mol, preferably from 1 to 1.1 mol, per mol of haloaromatic of the formula (II) and per Hal atom to be replaced.

Solvents employed are generally inert organic solvents. Well suited solvents are aromatic hydrocarbons such as toluene, xylenes, anisole, tetralin, and aliphatic ethers such as tetrahydrofuran, dimethoxyethane, ethylene glycol dimethyl ether, dioxane, tetrahydropyran and formaldehyde acetals. The reaction proceeds at temperatures of from 20 to 200° C., preferably at temperatures from 80 to 180° C., in particular from 100 to 150° C.

In the process of the invention, the amines are preferably reacted with haloaromatics in the presence of a strong base whose pKa is preferably >10. Bases which can be employed are, for example, alkali metal alkoxides or alkaline earth metal alkoxides, alkali metal amides or alkaline earth metal amides and also butyllithium or phenyllithium. Particularly preferred bases are alkali metal and alkaline earth metal alkoxides such as sodium tert-butoxide, potassium tert-butoxide, lithium tertbutoxide, sodium phenoxide or potassium phenoxide, potassium carbonate, sodium hexamethyldisilazide and lithium hexamethyldisilazide. Very particular preference is given to sodium tert-butoxide, potassium tert-butoxide and lithium tert-butoxide.

The base is preferably used in an amount of from 0.5 to 5 equivalents, in particular from 0.8 to 3 equivalents and very particularly preferably from 1 to 2 equivalents, based on the haloaromatic used.

The following examples serve to illustrate the process of the invention without restricting it thereto.

Synthesis of the Catalyst trans-Di-μ-acetatobis[2-[bis(1,1-dimethylethyl) phosphino]-2-methylpropyl-C,P]dipalladium(II)

5.10 mg (22.7 mmol) of Pd(OAc)$_2$ are dissolved in 200 ml of toluene. 5.00 mg (24.7 mmol) of tri(tert-butyl)phosphine are added to the solution. The solution, which quickly becomes a clear light orange, is heated at 70–80° C. for 10 minutes and is then cooled to room temperature. The solvent is removed under reduced pressure. After addition of 200 ml of hexane, the product, viz. trans-di-μ-acetatobis[2-[bis(1,1-dimethylethyl)phosphino]-2-methylpropyl-C,P] dipalladium, crystallizes out after a short time and is filtered off. This gives a whitish yellow solid (m.p.>200° C.). Recrystallization from hexane and filtration of the solutions through Celite® enables the product to be obtained in analytically pure form as whitish yellow crystalline needles.

EXAMPLES

Example 1

Preparation of 4-(N,N-diethylamino)toluene 20 mmol of p-chlorotoluene (2.53 g), 24 mmol of diethylamine (1.75 g), 28 mmol of KOtBu (3.13 g) and 44 mg of trans-di-μ-acetatobis[2-[bis(1,1-dimethylethyl)-phosphino]-2-methylpropyl-C,P]dipalladium(II) (0.3 mol %) are suspended in 50 ml of toluene and refluxed for 24 hours. After cooling to room temperature, the salts are filtered off and washed with petroleum ether. The solvents are removed from the filtrate on a rotary evaporator. Distillation via a bulb tube (100° C./12 torr) gives 4-(N,N-diethylamino) toluene as a colorless liquid in a yield of 87%.

Example 2

Preparation of 4-(N,N-diethylamino)toluene in the presence of LiBr 20 mmol of p-chlorotoluene (2.53 g), 24 mmol of diethylamine (1.75 g), 28 mmol of KOtBu (3.13 g), 4 mmol of lithium bromide (0.35 g) and 44 mg of trans-di-μ-acetatobis [2-[bis(1,1-dimethylethyl)phosphino]-2-methylpropyl-C,P] dipalladium(II) (0.3 mol %) are suspended in 50 ml of toluene and refluxed for 24 hours. After cooling to room temperature, the salts are filtered off and washed with petroleum ether. The solvents are removed from the filtrate on a rotary evaporator. Distillation via a bulb tube (100° C./12 torr) gives 4-(N,N-diethylamino)toluene as a colorless liquid in a yield of 91%.

Example 3

Preparation of 2,5-diphenyl-3-piperidinofuran 30 mmol of 2,5-diphenyl-3-chlorofuran (7.64 g), 32 mmol of freshly distilled piperidine (3.0 g), 32 mmol of KOtBu (3.6 g), 2 mmol of lithium chloride (42.5 mg) and 44 mg of trans-di-µ-acetatobis[2-[bis(1,1-dimethylethyl)phosphino]-2-methylpropyl-C,P]dipalladium(II) (0.2 mol %) are suspended in 50 ml of THF and placed in a pressure tube under protective gas. After 12 hours at 110° C., the tube is cooled to room temperature, the salts are filtered off and washed with petroleum ether. The solvents are removed from the filtrate on a rotary evaporator. Crystallization from 96% strength ethanol gives 2,5-diphenyl-3-piperidinofuran as a colorless solid; yield: 84%; melting point: 103° C.

Example 4

Preparation of N-cyclohexylaniline 30 mmol chlorobenzene (3.4 g), 31 mmol of freshly distilled cyclohexylamine (3.1 g), 31 mmol of KOtBu (3.5 g), 20 mmol of lithium chloride (0.85 g) and 23 mg of trans-di-µ-chlorobis[2-[bis(1,1-dimethylethyl)phosphino]-2-methylpropyl-C,P]dipalladium(II) (0.1 mol %) are suspended in 50 ml of ethylene glycol dimethyl ether and refluxed under protective gas for 9 hours. After cooling to room temperature, the salts are filtered and washed with petroleum ether. The solvents are removed from the filtrate under reduced pressure on a rotary evaporator. Distillation gives N-cyclohexylamine as a colorless liquid which has a boiling point of 133° C./65 torr, and crystallizes slowly on storage in a refrigerator; yield: 77%.

Example 5

Preparation of 1-(2,4-dimethylphenyl)imidazole 30 mmol of 2,4-dimethylchlorobenzene (4.2 g), 40 mmol of imidazole (2.7 g), 35 mmol of NaOEt solution in ethanol (10% by weight) and 230 mg of trans-di-µ-chlorobis[2-[bis(1,1-dimethylethyl)phosphino]-2-methylpropyl-C,P]dipalladium(II) (1.0 mol %) are suspended in 50 ml of THF and heated at 110° C. in a pressure tube for 9 hours. After removal of the salts by filtration, the solvent is removed under reduced pressure. This gives crude 1-(2,4-dimethylphenyl)imidazole as a brown liquid which can be purified by distillation (boiling point: 122° C./12 torr); yield: 48%.

Example 6

Preparation of N-(4-chlorophenyl)piperidine 15 mmol of p-dichlorobenzene (2.2 g), 15.5 mmol of piperidine (1.3 g), 15.5 mmol of NaOEt solution in ethanol (10% by weight) and 50 mg of trans-di-µ-chlorobis[2-[bis(1,1-dimethylethyl)phosphino]-2-methylpropyl-C,P]dipallium(II) are suspended in 75 ml of dioxane and refluxed for 15 hours. After aqueous work-up, extraction with petroleum ether and drying over sodium sulfate, the solvents are removed under reduced pressure. This gives crude N-(4-chlorophenyl)piperidine as a light brown liquid which can be purified by distillation (boiling point: 50° C./0.08 torr); melting point: 69° C.; yield: 59%.

Example 7

Preparation of 1,4-bis(N,N-dibutylamino)benzene 30 mmol of p-dichlorobenzene (4.4 g), 70 mmol of di-n-butylamine (9.0 g), 70 mmol of KOtBu (7.9 g), 30 mmol of lithium bromide (2.6 g) and 44 mg of trans-di-µ-acetatobis[2-[bis(1,1-dimethylethyl)phosphino]µ-2-methylpropyl-C,P]dipalladium(II) (0.2 mol %) are suspended in 75 ml of toluene and placed in a pressure tube under protective gas. After 12 hours at 140° C., an aqueous work-up is carried out. After the aqueous phase has been extracted twice with toluene, the combined organic phases are dried over magnesium sulfate and freed of the solvents on a rotary evaporator. Distillation gives 1,4-bis(N,N-dibutylamino)benzene as a virtually colorless liquid having a boiling point of 143° C./10 torr; yield: 77%.

What is claimed is:

1. Process for preparing aromatic amines of the formula (I)

where
n is 1, 2 or 3,
Ar is unsubstituted or substituted phenyl, furanyl, pyrryl, pyridinyl, naphthyl or quinolinyl, where the substituents are 1, 2, 3, 4, 5 or 6, in number and are selected from the group consisting of $C_1$–$C_8$-alkyl, $C_3$–$C_8$-cycloalkyl, $C_1$–$C_8$-alkoxy, $C_1$–$C_8$-acyloxy, $C_6$–$C_{10}$-aryloxy, $C_6$–$C_{10}$-aryl, benzyl, fluorine, chlorine, bromine, OH, $NO_2$, $OSO_2CF_3$, CN, COOH, CHO, $SO_3H$, $SO_2R$, SOR, where R is $C_1$–$C_4$-alkyl, $C_6$–$C_{10}$-aryl or benzyl, $NH_2$, NH—$C_1$–$C_8$-alkyl, N—($C_1$–$C_8$-alkyl)$_2$, $CF_3$, NHCO—$C_1$–$C_4$-alkyl, N—$C_1$–$C_4$-alkyl-CO—$C_1$–$C_4$-alkyl, COO—$C_1$–$C_8$-alkyl, $CONH_2$, CO—$C_1$–$C_8$-alkyl, NHCOH, NCOO—$C_1$–$C_4$-alkyl, CO-phenyl, COO-phenyl, CHCH—$CO_2$—$C_1$–$C_8$alkyl, $CHCHCO_2H$, PO-phenyl$_2$, PO—($C_1$–$C_4$-alkyl)$_2$, 5-membered heteroaryl and 6-membered heteroaryl in each case containing O, S and/or N as heteroatoms; and
$R^6$ and $R^7$ are, independently of one another, hydrogen, $C_1$–$C_{12}$-alkyl, $C_1$–$C_{12}$-hydroxyalkyl, unsubstituted or substituted phenyl, or $C_3$–$C_8$-cycloalkyl, or $R^6$ and $R^7$ together with the N atom form a 5- or 6-membered aliphatic or aromatic ring which may contain 1 or 2 further atoms selected from the group consisting of N, O and S as heteroatoms,
by reacting haloaromatics of the formula (II)

where Hal is Cl, Br or I,
with an amine of the formula (III)

wherein the reaction is carried out in the presence of a palladaphosphacyclobutane of the formula (IV)

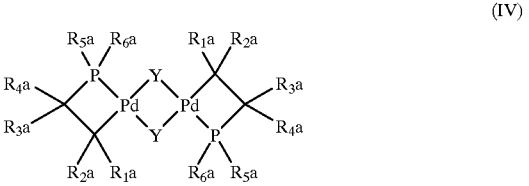

where
$R^{1a}$, $R^{2a}$ are, independently of one another, hydrogen, $C_1$–$C_4$-alkyl, $C_3$–$C_{12}$-cycloalkyl, $C_1$–$C_4$-alkoxy, fluorine, N—($C_1$–$C_4$-alkyl)$_2$, $CO_2$–$C_1$–$C_4$-alkyl, OCO—$C_1$–$C_4$-alkyl or substituted or unsubstituted aryl,
$R^{3a}$, $R^{4a}$, $R^{5a}$ and $R^{6a}$ are, independently of one another $C_1$–$C_8$-alkyl, $C_3$–$C_{12}$cycloalkyl, substituted or unsubstituted aryl;

or $R^{1a}$ and $R^{2a}$, or $R^{2a}$ and $R^{3a}$, or $R^{3a}$ and $R^{4a}$ together form an aliphatic ring having from 4 to 10 carbon atoms, or $R^{5a}$ and $R^{6a}$ together with the P atom form a saturated or unsaturated 4- to 9-membered ring, or $R^{4a}$ and $R^{5a}$ form a bridging 1,ω-alkanediyl chain having from 2 to 7 carbon atoms, and Y is an anion of an inorganic or organic acid, an α,γ-diketo compound or a 5- to 6-membered nitrogen-containing heterocycle, in the presence of a base and in the presence or absence of an ionic halide in a solvent at temperatures of from 20 to 200° C.

2. The process as claimed in claim 1, wherein $R^{1a}$ and $R^{2a}$ are, independently of one another, hydrogen, methyl, ethyl, cyclopentyl, cyclohexyl, methoxy, ethoxy, fluorine, phenyl, tolyl or naphthyl;

$R^{3a}$ and $R^{4a}$ are, independently of one another, $C_1-C_4$-alkyl, $C_5-C_6$-cycloalkyl, substituted or unsubstituted $C_6-C_{10}$-aryl or $R^{3a}$ and $R^{4a}$ together form an aliphatic ring having from 5 to 6 carbon atoms;

$R^{5a}$ and $R^{6a}$ are, independently of one another, $C_1-C_4$-alkyl, $C_5-C_6$-cycloalkyl, phenyl, naphthyl, anthracenyl, each of which may be unsubstituted or substituted by from 1 to 3 $CF_3$, $C_1-C_4$-alkyl or $C_1-C_4$-alkoxy groups;

and Y is acetate, propionate, benzoate, chloride, bromide, iodide, fluoride, sulfate, hydrogensulfate, nitrate, phosphate, trifluoromethanesulfonate, tetrafluoroborate, tosylate, mesylate, acetylacetonate, hexafluoroacetylacetonate or pyrazolyl.

3. The process as claimed in claim 1, wherein $R^{1a}$ and $R^{2a}$ are, independently of one another, hydrogen or methyl;

$R^{3a}$ and $R^{4a}$ are, independently of one another, methyl, ethyl or phenyl;

$R^{5a}$ and $R^{6a}$ are, independently of one another, phenyl, naphthyl, o-trifluoromethylphenyl, o-trifluoromethyl-p-tolyl, o-trifluoromethyl-p-methoxyphenyl, o-methoxyphenyl, o,p-dimethoxyphenyl, o,o,p-trimethoxyphenyl, anthracenyl, tert-butyl, n-butyl, isopropyl, isobutyl, cyclohexyl or 1-methylcyclohexyl.

4. The process as claimed in claim 1, wherein the compound of the formula (IV) is trans-di-μ-acetatobis[2-[bis(1,1-dimethylethyl)phosphino]-2-methylpropyl-C,P] dipalladium(II), trans-di-μ-acetatobis[2-[(1,1-dimethylethyl)-phenylphosphino]-2-methylpropyl-C,P] dipalladium(II), trans-di-μ-chlorobis[2-[bis(1,1-dimethylethyl)phosphino]-2-methylpropyl-C,P]dipalladium (II), trans-di-μ-chlorobis[2-[(1,1-dimethylethyl)-phenylphosphino]-2-methylpropyl-C,P]dipalladium(II), trans-di-μ-bromobis[2-[bis(1,1-dimethylethyl)phosphino]-2-methylpropyl-C,P]dipalladium(II) or trans-di-μ-bromobis[2-[(1,1-dimethylethyl)phenylphosphino]-2-methylpropyl-C,P]dipalladium(II).

5. The process as claimed in claim 1, wherein the compound of the formula (IV) is added as such.

6. The process as claimed in claim 1, wherein the compound of the formula (IV) is used in an amount of from 0.001 to 5 mol % based on the haloaromatic of the formula (II).

7. The process as claimed in claim 6, wherein the compound of the formula (IV) is used in an amount of from 0.01 to 0.9 mol % based on the haloaromatic of the formula (II).

8. The process as claimed in claim 1, wherein the haloaromatic has the formula (IIa), (IIb), (IIc) or (IId)

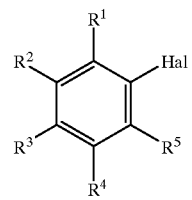

(IIa)

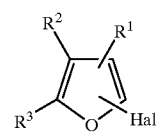

(IIb)

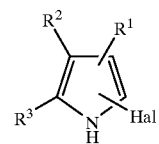

(IIc)

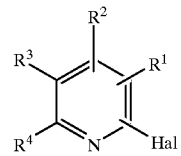

(IId)

where $R^1$ to $R^5$ are identical or different and are each hydrogen, $C_1-C_4$-alkyl, $C_5-C_6$-cycloalkyl, $C_1-C_4$-alkoxy, $C_1-C_6$-acyloxy, phenoxy, phenyl, fluorine, chlorine, OH, $NO_2$, CN, COOH, NH—$C_1-C_4$-alkyl, N($C_1-C_4$-alkyl)$_2$, COO—$C_1-C_4$-alkyl, CO—$C_1-C_4$alkyl, $CF_3$, $SO_3H$, $SO_2R$, where R is methyl, ethyl or phenyl.

9. The process as claimed in claim 1, wherein $R^6$ and $R^7$ are identical or different and are each hydrogen, $C_1-C_6$-alkyl, $C_1-C_6$-hydroxyalkyl, phenyl or $C_5-C_6$-cycloalkyl, or $R^6$ and $R^7$ together with the N atom form a piperazine, piperidine, morpholine, imidazole, pyrazole or pyrrolidine ring.

10. The process as claimed in claim 1, wherein the ionic halide is an alkali metal, ammonium, alkylammonium, alkylolammonium or phosphonium halide, where halide is chloride, bromide or iodide.

11. The process as claimed in claim 1, wherein the base is an alkali metal alkoxide or alkaline earth metal alkoxide, an alkali metal amide or alkaline earth metal amide, butyllithium, phenyllithium, lithium hexamethyldisilazide or sodium hexamethyldisilazide.

* * * * *